United States Patent
Breton et al.

(10) Patent No.: US 12,285,589 B2
(45) Date of Patent: Apr. 29, 2025

(54) INSULIN MONITORING AND DELIVERY SYSTEM AND METHOD FOR CGM BASED FAULT DETECTION AND MITIGATION VIA METABOLIC STATE TRACKING

(71) Applicant: UNIVERSITY OF VIRGINIA PATENT FOUNDATION, Charlottesville, VA (US)

(72) Inventors: Marc D. Breton, Charlottesville, VA (US); Stephen D. Patek, Charlottesville, VA (US); Boris P. Kovatchev, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 0 days.

(21) Appl. No.: 18/599,531

(22) Filed: Mar. 8, 2024

(65) Prior Publication Data
US 2024/0245849 A1   Jul. 25, 2024

Related U.S. Application Data

(63) Continuation of application No. 17/694,870, filed on Mar. 15, 2022, now Pat. No. 11,951,278, which is a
(Continued)

(51) Int. Cl.
*A61M 5/142* (2006.01)
*A61B 5/00* (2006.01)
(Continued)

(52) U.S. Cl.
CPC ......... *A61M 5/142* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

| | | |
|---|---|---|
| 6,923,763 B1 | 8/2005 | Kovatchev et al. |
| 7,025,425 B2 | 4/2006 | Kovatchev et al. |
| (Continued) | | |

FOREIGN PATENT DOCUMENTS

| | | |
|---|---|---|
| WO | 0113786 A1 | 3/2001 |
| WO | 0172208 A2 | 10/2001 |
| (Continued) | | |

OTHER PUBLICATIONS

International Search Report (PCT/ISA/210) mailed on Sep. 23, 2016, by the Korean Patent Office as the International Searching Authority for International Application No. PCT/US2016/036729.
(Continued)

*Primary Examiner* — Michael R Bloch
(74) *Attorney, Agent, or Firm* — Buchanan Ingersoll & Rooney PC

(57) ABSTRACT

An insulin monitoring system includes one or more processors, one or more computer-readable storage devices, and program instructions stored on at least one of the one or more storage devices for execution by at least one of the one or more processors. The program instructions include: first program instructions to track, in real time, the amount of insulin active in a patient; second program instructions to calculate the amount of insulin need of the patient by tracking the patient's metabolic states; third program instructions to compare the insulin active in the patient with the insulin need of the patient; and fourth program instructions to determine an insulin fault level based on the comparison.

27 Claims, 10 Drawing Sheets

Related U.S. Application Data continuation of application No. 15/580,935, filed as application No. PCT/US2016/036729 on Jun. 9, 2016, now Pat. No. 11,311,665.

(60) Provisional application No. 62/173,080, filed on Jun. 9, 2015.

(51) Int. Cl.
| | | |
|---|---|---|
| *A61B 5/145* | (2006.01) | |
| *A61M 5/168* | (2006.01) | |
| *A61M 5/172* | (2006.01) | |
| *G16H 10/65* | (2018.01) | |
| *G16H 20/17* | (2018.01) | |
| *G16H 40/60* | (2018.01) | |
| *G16H 40/63* | (2018.01) | |
| *G16H 50/20* | (2018.01) | |

(52) U.S. Cl.
CPC ............ *A61B 5/486* (2013.01); *A61B 5/4866* (2013.01); *A61B 5/7275* (2013.01); *A61B 5/746* (2013.01); *A61M 5/168* (2013.01); *A61M 5/172* (2013.01); *A61M 5/1723* (2013.01); *G16H 10/65* (2018.01); *G16H 20/17* (2018.01); *G16H 40/60* (2018.01); *G16H 40/63* (2018.01); *G16H 50/20* (2018.01); *A61M 2005/14208* (2013.01); *A61M 2205/18* (2013.01); *A61M 2205/3576* (2013.01); *A61M 2205/502* (2013.01); *A61M 2205/507* (2013.01)

(56) References Cited

U.S. PATENT DOCUMENTS

| | | | |
|---|---|---|---|
| 7,204,823 B2 | 4/2007 | Estes et al. | |
| 7,651,489 B2 | 1/2010 | Estes et al. | |
| 7,815,569 B2 | 10/2010 | Kovatchev et al. | |
| 7,837,647 B2 | 11/2010 | Estes et al. | |
| 7,874,985 B2 | 1/2011 | Kovatchev et al. | |
| 8,012,119 B2 | 9/2011 | Estes et al. | |
| 8,135,548 B2 | 3/2012 | Breton et al. | |
| 8,500,702 B2 | 8/2013 | Estes et al. | |
| 8,538,703 B2 | 9/2013 | Kovatchev et al. | |
| 8,562,587 B2 | 10/2013 | Kovatchev et al. | |
| 8,585,593 B2 | 11/2013 | Kovatchev et al. | |
| 8,718,943 B2 | 5/2014 | Moerman | |
| 8,718,958 B2 | 5/2014 | Breton et al. | |
| 8,924,160 B2 | 12/2014 | Moerman | |
| 8,924,161 B2 | 12/2014 | Moerman | |
| 8,924,180 B2 | 12/2014 | Nishikawa et al. | |
| 2003/0028089 A1* | 2/2003 | Galley ............... | A61B 5/14532 128/920 |
| 2003/0114836 A1 | 6/2003 | Estes et al. | |
| 2003/0114838 A1 | 6/2003 | Oneill et al. | |
| 2004/0248204 A1 | 12/2004 | Moerman | |
| 2005/0245904 A1 | 11/2005 | Estes et al. | |
| 2007/0083335 A1 | 4/2007 | Moerman | |
| 2007/0083336 A1 | 4/2007 | Huang et al. | |
| 2007/0287985 A1 | 12/2007 | Estes et al. | |
| 2008/0154101 A1 | 6/2008 | Jain et al. | |
| 2008/0154513 A1 | 6/2008 | Kovatchev et al. | |
| 2008/0269714 A1* | 10/2008 | Mastrototaro ..... | A61B 5/14865 604/504 |
| 2008/0314385 A1 | 12/2008 | Brunner et al. | |
| 2008/0314395 A1 | 12/2008 | Kovatchev et al. | |
| 2009/0171589 A1 | 7/2009 | Kovatchev | |
| 2009/0209938 A1 | 8/2009 | Aalto-setaelae | |
| 2010/0179768 A1 | 7/2010 | Kovatchev et al. | |
| 2010/0198520 A1 | 8/2010 | Breton et al. | |
| 2010/0295686 A1* | 11/2010 | Sloan ................... | G16H 20/17 703/2 |
| 2011/0028901 A1 | 2/2011 | Estes et al. | |
| 2011/0029269 A1* | 2/2011 | Hayter ............... | A61M 5/1723 702/104 |
| 2011/0034791 A1 | 2/2011 | Moerman | |
| 2011/0034793 A1 | 2/2011 | Moerman | |
| 2011/0046051 A1 | 2/2011 | Moerman | |
| 2011/0046468 A1 | 2/2011 | Moerman | |
| 2011/0046892 A1 | 2/2011 | Moerman | |
| 2011/0046895 A1 | 2/2011 | Moerman | |
| 2011/0264374 A1 | 10/2011 | Johnson et al. | |
| 2011/0264378 A1 | 10/2011 | Breton et al. | |
| 2011/0295341 A1 | 12/2011 | Estes et al. | |
| 2012/0004512 A1 | 1/2012 | Kovatchev et al. | |
| 2012/0035547 A1 | 2/2012 | Estes et al. | |
| 2012/0041414 A1 | 2/2012 | Estes et al. | |
| 2012/0041415 A1 | 2/2012 | Estes et al. | |
| 2012/0078067 A1 | 3/2012 | Kovatchev et al. | |
| 2012/0130698 A1 | 5/2012 | Kovatchev et al. | |
| 2012/0191361 A1 | 7/2012 | Kovatchev et al. | |
| 2012/0245556 A1 | 9/2012 | Kovatchev et al. | |
| 2013/0079613 A1 | 3/2013 | Kovatchev et al. | |
| 2013/0116649 A1 | 5/2013 | Breton et al. | |
| 2013/0165901 A1 | 6/2013 | Ruchti et al. | |
| 2013/0338629 A1* | 12/2013 | Agrawal ............. | A61B 5/4839 600/365 |
| 2014/0046159 A1 | 2/2014 | Kovatchev et al. | |
| 2014/0046169 A1 | 2/2014 | Liu et al. | |
| 2014/0215239 A1 | 7/2014 | Kovatchev et al. | |
| 2014/0244216 A1 | 8/2014 | Breton et al. | |
| 2014/0244218 A1 | 8/2014 | Greenberg et al. | |
| 2015/0018633 A1 | 1/2015 | Kovachev et al. | |
| 2015/0018833 A1 | 1/2015 | Crandall et al. | |
| 2015/0190098 A1 | 7/2015 | Patek et al. | |
| 2015/0193589 A1 | 7/2015 | Ortiz et al. | |
| 2019/0254595 A1 | 8/2019 | Breton et al. | |
| 2022/0203020 A1 | 6/2022 | Breton et al. | |

FOREIGN PATENT DOCUMENTS

| | | |
|---|---|---|
| WO | 02067776 A1 | 9/2002 |
| WO | 2005106017 A2 | 11/2005 |
| WO | 2007027691 A1 | 3/2007 |
| WO | 2007081853 A2 | 7/2007 |
| WO | 2008052199 A2 | 5/2008 |
| WO | 2008067284 A2 | 6/2008 |
| WO | 2008157781 A1 | 12/2008 |
| WO | 2009009528 A2 | 1/2009 |
| WO | 2010062898 A1 | 6/2010 |
| WO | 2010099313 A1 | 9/2010 |
| WO | 2010138848 A1 | 12/2010 |
| WO | 2010151834 A1 | 12/2010 |
| WO | 2011028731 A1 | 3/2011 |
| WO | 2011028925 A1 | 3/2011 |
| WO | 2011112974 A1 | 9/2011 |
| WO | 2011119832 A1 | 9/2011 |
| WO | 2012178113 A1 | 12/2012 |
| WO | 2012178134 A2 | 12/2012 |
| WO | 2013032965 A1 | 3/2013 |
| WO | 2013177565 A1 | 11/2013 |
| WO | 2014022864 A1 | 2/2014 |
| WO | 2014130841 A1 | 8/2014 |
| WO | 2015003124 A2 | 1/2015 |
| WO | 2015021441 A1 | 2/2015 |
| WO | 2015103543 A1 | 7/2015 |

OTHER PUBLICATIONS

Written Opinion (PCT/ISA/237) mailed on Sep. 23, 2016, by the Korean Patent Office as the International Searching Authority for International Application No. PCT/US2016/036729.

* cited by examiner

INSULIN MONITORING AND DELIVERY SYSTEM AND METHOD FOR CGM BASED FAULT DETECTION AND MITIGATION VIA METABOLIC STATE TRACKING

CROSS REFERENCE TO RELATED APPLICATIONS

This application claims priority under 35 U.S.C. 119(c) to U.S. Provisional Application Ser. No. 62/173,080, filed Jun. 9, 2015 entitled "CGM BASED FAULT DETECTION AND MITIGATION OF INSULIN DELIVERY/MONITORING SYSTEMS VIA METABOLIC STATE TRACKING," the disclosure of which is incorporated by reference herein in its entirety.

STATEMENT REGARDING FEDERALLY SPONSORED RESEARCH OR DEVELOPMENT

This invention was made with government support under Grant No. DK085623, awarded by the National Institutes of Health. The government has certain rights in the invention.

BACKGROUND

Insulin is commonly produced by the human body to help balance blood sugar levels. Some people's bodies, however, do not produce the right amounts of insulin. This can cause medical complications in the body of not addressed properly. Thus, some people may need to deliver insulin to their bodies in order to avoid such medical complications.

A person may choose to deliver insulin to one's body using one of several known systems and methods, including using a syringe, an injection pen, or with an insulin pump. However, existing systems and methods for delivering insulin may not be accurate in delivering the amount of insulin actually needed by a body. Or it may be tedious and time consuming to accurately deliver the actual needed amount of insulin using existing systems and methods. Delivering an inaccurate amount of insulin may result in medical complications.

SUMMARY

An example two-phase 3-tier system, method, and computer readable medium aimed at detecting and potentially remedying inappropriate insulin delivery in diabetic patients (or applicable subjects) is described herein.

In a first phase, the system (and the related method and computer readable medium) detects under-insulinization by tracking in real time the insulin that is active or to be active, in a patient (Insulin on Board or "IOB"), while frequently, but not necessarily regularly, comparing it to the insulin need of the patient (Insulin that Should be On Board or "ISOB"). ISOB is determined by tracking the patient metabolic states. For example, but not limited thereto, ISOB is determined using measures related to his/her glycemia and/or metabolic states related to glycemic response to insulin such as but not restricted to plasma and capillary insulin concentration, physical activity indicators, e.g. heart rate or movement, and insulin sensitivity modifier such as stress, fever, etc.

In a second phase, the system (and related method) determines if a detected lack of active insulin can be remedied with the current insulin delivery/monitoring system, or if a fault exists that requires external intervention on the delivery/monitoring system. In the first case, based on the previous assessment, the system (and related method) can then either (i) alert the patient for the need of additional insulin and advise on a temporary basal rate, or (ii) safely, and over a period of time, replenish the IOB by automatically increasing insulin delivery until ISOB matches IOB. It is noted that the patient's need in insulin may fluctuate during the day based on disturbances to their metabolism and/or different glycemic control goals.

In one example embodiment, the system alerts the patient of a severe fault with the delivery/monitoring system and guides the patient in identifying and remedying the detected fault.

DETAILED DESCRIPTION

Throughout an exemplary, non-limiting embodiment, the system informs the user of the level of fault detection as follows:

Green: no under delivery of insulin detected
Yellow: Under-delivery can be remedied using the current delivery/monitoring device
Red: Severe under-delivery due to delivery/monitoring system malfunction.

Figure 1:
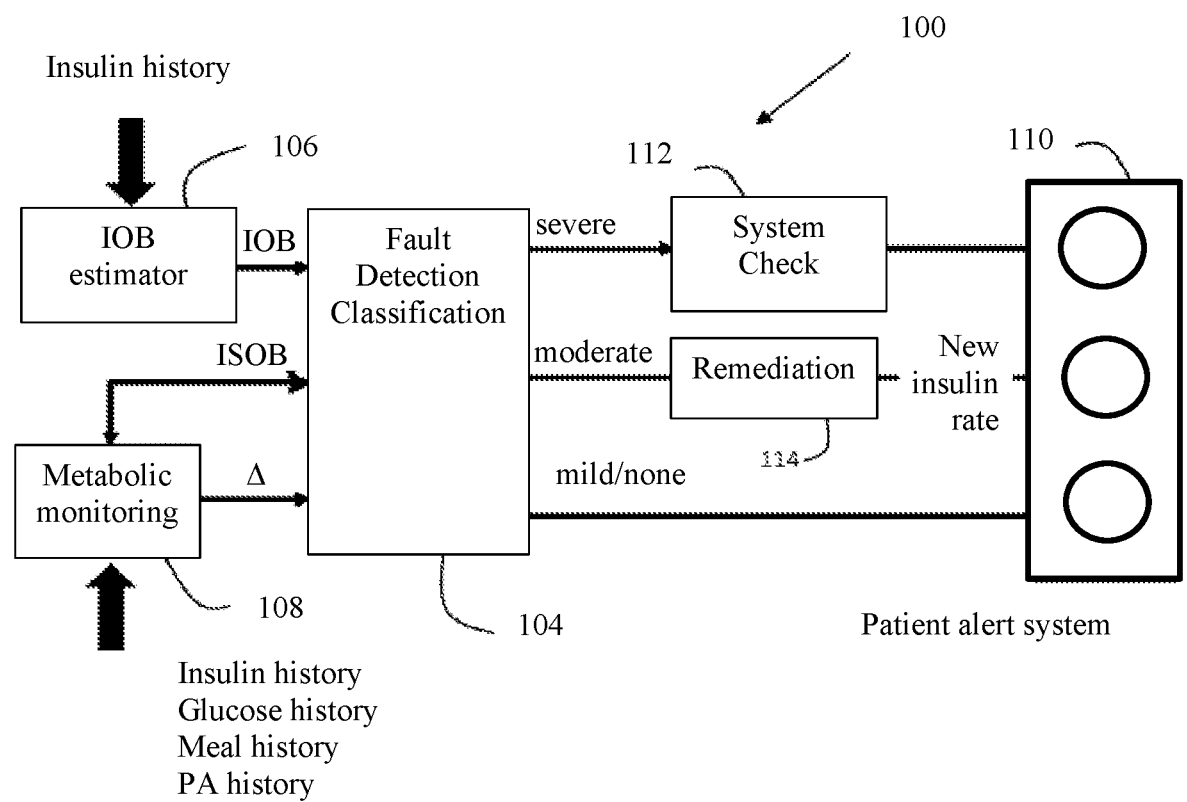
FIG. 1 illustrates an example IOB based insulin delivery and monitoring system.

FIG. 1 illustrates an example IOB based insulin delivery and monitoring system 100. The system 100 includes a Fault Detection and Classification module 104 for tracking in real time the insulin that is active or to be active, in a patient ("IOB") and comparing it to the insulin need of the patient ("ISOB"). The system 100 includes an IOB Estimator module 106 for providing the Fault Detection and Classification module 104 with IOB values. The system 100 further includes a Metabolic Monitoring module 108 for providing the Fault Detection and Classification module 104 with ISOB values. The Fault Detection and Classification module 104 compares the IOB value with the ISOB value to determine and classify the level of fault (green, yellow, or red, for example). In one example, the system 100 includes a notification module 110 to notify a user or patient of the determined fault level. It should be appreciated that the notification module 110 can be any suitable hardware or software module for conveying information to the user, such as a display, an audible alert, and so on. In one example, the system 100 includes a system check module 112 for per forming a System Check in the event that sever under-delivery is detected. In one example, the system 100 includes a Remediation module 114, for performing a remediation in the event that a determination is made that the under-delivery can be remedied using the current delivery/monitoring device.

then run from the last estimation) or on-demand (i.e. a large history, such as 6-8 h, is fed to the system that retains no initial memory—$X_0$ is set to a predetermined initial value). Below is one example implementation of an embodiment of an IOB estimator 106, including variables illustrated in Table 1 and calculations used.

TABLE 1

Example variables used by the IOB Estimator

| Name | Description | Units | type | | | |
|---|---|---|---|---|---|---|
| *Inputs* | | | | | | |
| J | a vector of past insulin injection in 5 min increments | U | 1 × 24 array of floats no empty allowed | | | |
| Time | absolute time at execution time | Seconds | UNIX datetime | | | |
| basal_hist | a vector of past basal rates in 5 min increments | U/hr | 1 × 24 array of floats no empty allowed | | | |
| *Outputs* | | | | | | |
| IOB | insulin on board | U | float | | | |
| *parameters* | | | | | | |
| INS_A | transfer matrix for insulin model | NA | 4 × 4 array of floats fixed at | | | |
| | | | 0.9048 | 6.255e−6 | 1.98e−8 | 3.994e−8 |
| | | | 0 | 0.4107 | 3.503e−3 | 7.104e−3 |
| | | | 0 | 0 | 0.9048 | 4.524e−2 |
| | | | 0 | 0 | 0 | 0.9048 |
| INS_B | input matrix for insulin model | NA | 4 × 1 array of float fixed at 7.241e−8 0.0207 0.117 4.758 | | | |
| CLEAR_C | output-state matrix for insulin model | NA | 4 × 4 array of float fixed at | | | |
| | | | 0 | 0 | 0.178 | 0 |
| CLEAR_D | output-input matrix for insulin model | NA | 4 × 1 array of float fixed at 0 | | | |

Instantiations

IOB Estimation

It should be appreciated that the IOB Estimator 106 can be configured to compute IOB using different methods. In one example, the IOB Estimator 106 is configured to compute IOB using the estimation of the amount of cleared insulin (insulin that has been degraded by the body or cleared from the central circulation). Removing this quantity from the amount of previously injected insulin one can get an estimate of how much insulin is active and/or will be active in the future. In an aspect of an embodiment of the present invention, IOB is understood as differential from a basal rate: a real (as implemented in an insulin pump) or virtual (e.g. in multiple daily injection therapeutics) insulin infusion rate that is designed to keep a diabetic patient in glycemic range, absent large perturbations (such as meals or exercise). Insulin clearance (the rate at which insulin is cleared at any point in time) can be modulated per patient or representative of a population average. In this instantiation, this is controlled by the INS_A, INS_B, CLEAR_C, and CLEAR_D matrices described below. The present inventors propose a discrete state space model representation of the IOB system. Such an implementation can be run recursively (i.e. Xk is kept in memory until the next estimation which Computation:

J is corrected for the basal insulin infusion (basal_hist):

$$\text{J\_diff}_k = J_k - \frac{\text{basal\_hist}_k}{12} \quad \text{Equ (1)}$$

The IOB estimator 106 computes the IOB by estimating the total (corrected) insulin that is infused so far minus the total insulin that has been cleared from the circulation. To get this estimate, the corrected infusion $u_1$ is transformed in two ways:

1. The total injected is updated every 5 minutes as:

$$\text{total}_{k+1} = \text{total}_k + \text{J\_diff}_k \quad \text{Equ (2)}$$

2. the total cleared insulin is updated every 5 minutes as:

$$\text{cleared}_k = \text{Clear\_C} \times X_k + \text{Clear\_D} \times \text{J\_diff}_k \quad \text{Equ (3)}$$

$$X_{k+1} = \text{INS\_A} \times X_k + \text{INS\_A} \times \text{J\_diff}_k$$

$$\text{total\_cleared}_{k+1} = \text{total\_cleared}_k + \text{cleared}_k$$

3. IOB is then computed as $$IOB_{k+1} = \text{total}_{k+1} - \text{total\_cleared}_k \quad \text{Equ (4)}$$

Metabolic Monitoring
Metabolic State Estimation

Here the present inventors propose to determine, among other things, the existence of faults in a meal/insulin/continuous glucose monitoring (CGM) informed system in diabetes. One of the key ideas, among others, is that careful monitoring of the capacity of a core Kalman Filter ("KF") estimation model to the received data can enable informing the user of the validity/safety of the overall system using the KF estimation.

Figure 2:
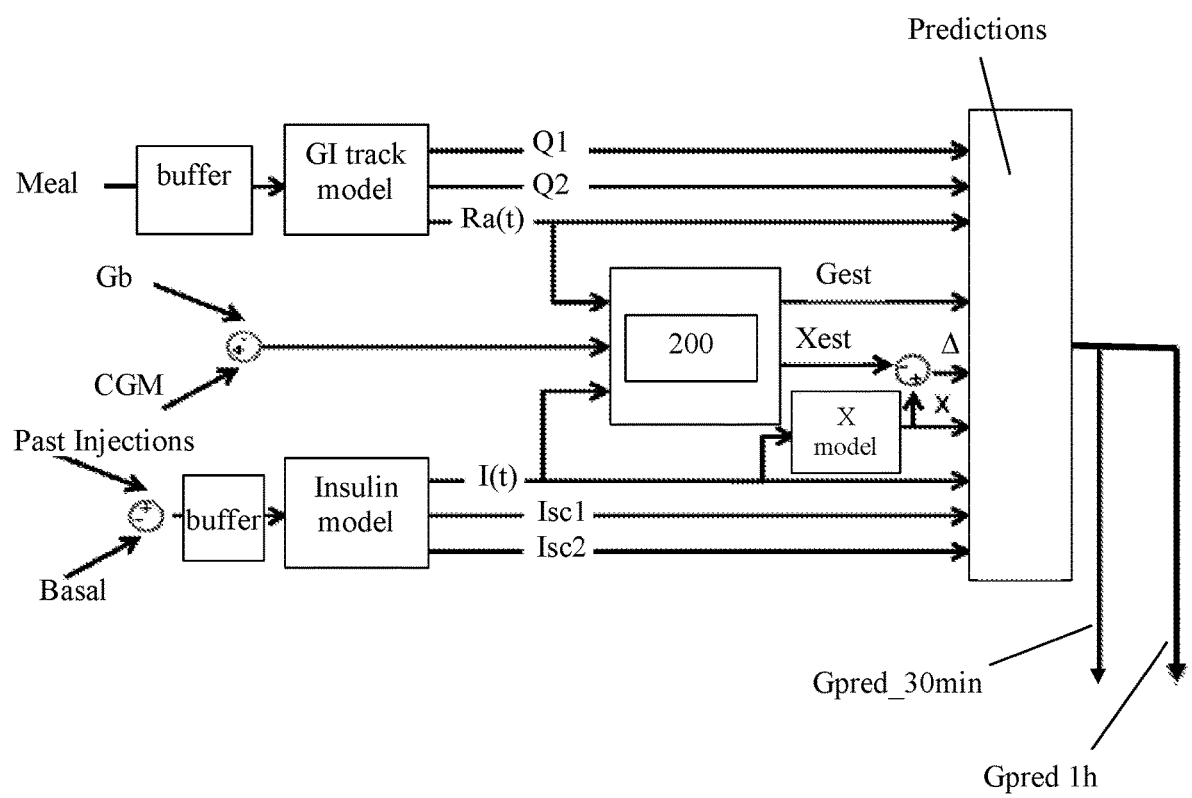
FIG. 2 illustrates an example Kalman filter.

Referring to FIG. 2, in particular, in one example, the Metabolic Monitoring module 108 is configured to compute at given intervals (every 5 minutes, for example) an estimate of the patient metabolic status using a Kalman filter 200. Contrary to previously proposed systems, Meal carbohydrate ("CHO") appearance and Plasma insulin are treated as feed-forward signals (i.e. they are considered fully known and are derived respectively from the meals and past insulin injections). These two signals are fed into the Kalman filter 200 as inputs, in addition to the CGM values. The Kalman filter then estimates two states: the plasma glucose and the insulin action.

The following is a listing of reference characters for FIG. 2:

Meal=last meal (see Table 2)
Buffer=insulin buffer
GI Model=This is the GI track system defined below
Q1=M_s_out$_k$ (3) discussed below
Q2=M_s_out$_k$ (2) discussed below
Ra(t)=Ra$_k$ discussed below
Gest=plasma glucose level estimation (see Table 2)
Xest=KFout$_k$(2) discussed below
Delta=see Equ(9) below
I(t)=I$_k$ discussed below
Xmodel=the first line in the matrix operation described in Equ(6), which corresponds to the Insulin System.
X=Xpred$_k$ discussed below
Insulin model=Istate$_k$ discussed below
ISC$_1$=Iout$_k$(4)
ISC$_2$=Iout$_k$(3)
Gpred_30 min=Plasma glucose 30 min prediction
Gpred_1 h=Plasma glucose 1 h prediction (see Table 2)
Gb=Gop (see Table 2)
Past injections—past injections
Basal=amount of basal insulin
CGM=CGM (see Table 2)

The estimated state is the used to forecast the metabolic state of the patient ahead, assuming no additional disturbance; a forecast that can be used in the ISOB computation.

In addition, the difference between the feed-forward insulin action (X) and the KF estimated insulin action (Xest) can form the basis for the severe fault detection system.

Table 2 illustrates example variables used by the Kalman filter 200 to estimate of the patient metabolic status.

TABLE 2

Example variables used by the Metabolic Monitoring Module

| Name | Description | units | type |
|---|---|---|---|
| inputs | | | |
| CGM | a vector of the past 2 h of CGM values in 5 min increments | mg/dl | 1 × 24 array of floats [40-400] empty value: −1 |
| J | a vector of past insulin injection in 5 min increments | U | 1 × 24 array of floats no empty allowed |
| Meal | described the last meal | NA | structure containing the following fields: time—UNIX datetime glucose—SMBG meas.—float CHO—float type—int 0 (slow) 1 (medium) 2 (fast) treated—Boolean active—Boolean if no meal yet set fields to [0; 0; 0; TRUE; FALSE] |
| Time | absolute time at execution time | seconds | UNIX datetime |
| EX | level of exercise | NA | Float [0 1] |
| basal | basal rate value at execution time | U/hr | float [0-3] |

TABLE 2-continued

Example variables used by the Metabolic Monitoring Module

| Name | Description | units | type |
|---|---|---|---|
| basal_hist | a vector of past basal rates in 5 min increments | U/hr | 1 × 24 array of floats no empty allowed |
| CF | Correction Factor at execution time | $mg \cdot dl^{-1} \cdot U^{-1}$ | float [10-100] |
| CR | Carbohydrate ration at execution time | $U \cdot g^{-1}$ | float [5-50] |
| BW | patient's weight | Kg | float [20-200] | outputs

| Name | Description | units | type |
|---|---|---|---|
| Const | Safety System constraint | $U \cdot hr^{-1}$ | float [0 3] |
| Gest | plasma glucose level estimation | mg/dl | float [20 400] |
| Gpred_1h | Plasma glucose 1 h prediction | mg/dl | float [20 400] |
| Gpred_light | Plasma glucose 10 min prediction with no insulin assumption for red light | mg/dl | float [20 400] | parameters

| Name | Description | units | type | | | |
|---|---|---|---|---|---|---|
| Gop | operation point glucose for kalman filter in KALMAN | mg/dl | float fixed at 90 | | | |
| INS_A | transfer matrix for insulin model | NA | 4 × 4 array of floats fixed at | | | |
| | | | 0.9048 | 6.256e−6 | 1.498e−6 | 3.023e−6 |
| | | | 0 | −0.4107 | 0.2651/BW | 0.5376/BW |
| | | | 0 | 0 | 0.9048 | 0.0452 |
| | | | 0 | 0 | 0 | 0.9048 |
| INS_B | input matrix for insulin model | NA | 4 × 1 array of float fixed at | | | |
| | | | 5.4793e−6/BW | | | |
| | | | 1.5661/BW | | | |
| | | | 0.1170 | | | |
| | | | 4.7581 | | | |
| INS_C | output-state matrix for insulin model | NA | 4 × 4 array of float fixed at | | | |
| | | | 1 | 0 | 0 | 0 |
| | | | 0 | 1 | 0 | 0 |
| | | | 0 | 0 | 1 | 0 |
| | | | 0 | 0 | 0 | 1 |
| INS_D | output-input matrix for insulin model | NA | 4 × 1 array of float fixed at | | | |
| | | | 0 | | | |
| | | | 0 | | | |
| | | | 0 | | | |
| | | | 0 | | | |
| MEAL_A | transfer matrix for meal model | NA | 2 × 2 array of floats fixed at | | | |
| | | | 0.9048 | | 0.04524 | |
| | | | 0 | | 0.9048 | |

TABLE 2-continued

Example variables used by the Metabolic Monitoring Module

| Name | Description | units | type |
|---|---|---|---|
| MEAL_B | input matrix for meal model | NA | 2 × 1 array of float fixed at<br>0.117<br>4.758 |
| MEAL_C | output-state matrix for meal model | NA | 3 × 2 array of float fixed at<br>0.02    0.01<br>1       0<br>0       1 |
| MEAL_D | output-input matrix for meal model | NA | 3 × 1 array of float fixed at<br>0<br>0<br>0 |
| CORE_pred_A | prediction matrix for core model | NA | 8 × 8 array of floats fixed at<br>0.5488  −1.9972e3  −1.4818e3  0.1733/BW  0.1127/BW  −0.0148   −0.0186/BW<br>0       0.9704     0          0          0          0         0<br>0       0          0.5488     0          0          6.89e−6   1.75e−5/BW<br>0       0          0          0.5488     0.1646     0         0<br>0       0          0          0          0.5488     0         0<br>0       0          0          0          0          0.0048    0.4315/BW<br>0       0          0          0          0          0         0.5488<br>0       0          0          0          0          0         0.1646 |
| CORE_pred_C | output matrix for core model | NA | 1 × 8 array of floats fixed at<br>1  0  0  0  0  0  0  0 |
| LIGHT_pred_A | prediction matrix for red light | NA | 8 × 8 array of floats fixed at<br>0.8187  −811.5  −736.85  0.08618/BW  0.0474/BW  −4.6399e<br>0       0.99    0        0           0          0<br>0       0       0.8187   0           0          8.229e−0<br>0       0       0        0.8187      0.08187    0<br>0       0       0        0           0.8187     0<br>0       0       0        0           0          0.16864<br>0       0       0        0           0          0<br>0       0       0        0           0          0 |
| LIGHT_pred_B | input matrix for red light model | | 8 × 2 array of floats fixed at<br>0.2457/BW        −42499e−3/BW<br>0                0<br>0                1.8075e−05/BW<br>0.4381           0<br>9.0635           0<br>0                2.5279/BW<br>0                9.0635<br>0                0.4381 |
| LIGHT_pred_C | output matrix for red light model | | 1 × 8 array of floats fixed at<br>1  0  0  0  0  0  0  0 |
| 1H_predA | 1 hour prediction matrix | | 8 × 8 array of floats fixed at<br>30.119  −3034.3E  −1626.4   0.19023/BW  0.1522/BW<br>0       0.94176    0         0           0<br>0       0          0.3.0119   0           0<br>0       0          0         0.30119     0.18072<br>0       0          0         0           0.30119<br>0       0          0         0           0<br>0       0          0         0           0<br>0       0          0         0           0 |
| 1H_pred_C | | | 1 × 8 array of floats fixed at<br>1  0  0  0  0  0  0  0 |
| KF_A | transfer matrix for kalman filter | NA | 4 × 4 array of floats fixed at<br>0.006        −407.177<br>0.0007       0.9048 |

TABLE 2-continued

Example variables used by the Metabolic Monitoring Module

| Name | Description | units | type |
|---|---|---|---|
| | | | 4 × 3 array of float fixed at |
| KF_B | input matrix for kalman filter | NA | −0.0021    2.5043/BW    0.8988<br>9.5163e−6    0    −7.3045e−4 |
| | | | 4 × 4 array of float fixed at |
| KF_C | output-state matrix for kalman filter | NA | 0.3699    0<br>8.0728e−4    1 |
| | | | 4 × 1 array of float fixed at |
| KF_D | output-input matrix for meal kalman filter | NA | 0    0    0.6301<br>0    0    −8.0728e−4 |
| | | | 2 × 2 array of float fixed at |
| BUFF_A | transfer matrix for meal and insulin buffers | NA | 0.9512    0.04756<br>0    0.9512 |
| | | | 2 × 1 array of float fixed at |
| BUFF_B | transfer matrix for meal and insulin buffers | NA | 1.209e−3<br>4.877e−2 |
| | | | 1 × 2 array of float fixed at |
| BUFF_C | transfer matrix for meal and insulin buffers | NA | 1    0 |
| | | | 1 × 1 array of float fixed at |
| BUFF_D | transfer matrix for meal and insulin buffers | NA | 0 |

Computation

1. First, the construction of the feedforward model outputs is performed (green, for example). It should be appreciated that this code is recursive and needs to be run at certain intervals (every 5 minutes, for example). If an execution during an interval is missed, then the code may be run for each interval since the last execution:

GI Track System

The calculation for GI track system can be defined as follows:

```
If Time-Meal.time<300
    meal_amount_k=1000*Meal.CHO/5
else
    meal_amount_k=0;
end
```

Thus, $$Mbuf_k = \text{BUFF\_A} \times Mbuf_k + \text{BUFF\_B} \times \text{meal\_amount}_k \quad \text{Equ (5)}$$

$$\begin{cases} Mout_k = \text{MEAL\_C} \times Mstate_k + \text{MEAL\_D} \times Mbuf_k \\ Mstate_{k+1} = \text{MEAL\_A} \times Mstate_k + \text{MEAL\_B} \times Mbuf_k \end{cases}$$

$$Ra_k = Mout_k(1)$$

$$\text{M\_s\_out}_k = \begin{bmatrix} Mout_k(2) \\ Mout_k(3) \end{bmatrix}$$

Insulin System

The calculation for Insulin system can be defined as follows:

$$Ibuf_k = \text{BUFF\_A} \times Ibuf_k + \text{BUFF\_B} \times (J_k - \text{basal\_hist}_k) \quad \text{Equ (6)}$$

$$\begin{cases} Iout_k = \text{INS\_C} \times Istate_k + \text{INS\_D} \times Ibuf_k \\ Istate_{k+1} = \text{INS\_A} \times Istate_k + \text{INS\_B} \times Ibuf_k \end{cases}$$

$$I_k = Iout_k(2)$$

-continued $$Xpred_k = Iout_k(1)$$

$$I\_s\_out_k = \begin{bmatrix} Iout_k(3) \\ Iout_k(4) \end{bmatrix}$$

2. The Kalman Filter estimate is next computed. It should be appreciated that this code is recursive and needs to be run at certain intervals (every 5 minutes, for example). If an execution during an interval is missed, then the code may be run for each interval since the last execution:

$$\begin{cases} KFout_k = KF\_C \times KFstate_k + KF\_D \times \begin{bmatrix} I_k \\ Ra_k \\ CGM_k - Gop \end{bmatrix} \\ KFstate_{k+1} = KF\_A \times KFstate_k + KF\_B \times \begin{bmatrix} I_k \\ Ra_k \\ CGM_k - Gop \end{bmatrix} \end{cases} \quad \text{Equ (7)}$$

3. Output variable Gest and Delta are next created:

$$Gest = KFout_k(1) + Gop \quad \text{Equ(8)}$$

$$Delta = KFout_k(2) - Xpred_k \quad \text{Equ(9)}$$

4. The predictions are then made:

$$XI_k = \begin{bmatrix} KFout_k(1) \\ Delta \\ Xpred_k \\ I_k \\ I\_s\_out_k(1) \\ I\_s\_out_k(2) \\ M\_s\_out_k(1) \\ M\_s\_out_k(2) \end{bmatrix} \quad (10)$$

$$Gpred = CORE\_pred\_C \times CORE\_pred\_A \times XI_k + Gop$$

$$Gpred\_light = LIGHT\_pred\_C \times$$

$$(LIGHT\_pred\_A \times XI_k + LIGHT\_pred\_B \times [-basal, 0]) + Gop$$

$$Gpred\_1h = 1h\_pred\_C \times 1h\_pred\_A \times XI_k + Gop$$

Insulin that should be on Board (ISOB) Computation

The Metabolic Monitoring module 108 is further configured to compute insulin need of a patient. It should be appreciated that the Metabolic Monitoring module 108 may be configured to compute insulin need of a patient, or ISOB, in a multitude of ways: it can be estimated based on past measurements (e.g. glycemia, insulin, heart rate, accelerometry, temperature . . . ), as described herein, or it could even be directly measured (in which case this module would be inactive and it would feed directly in the Advice Rate Computation Module below).

Figure 3:
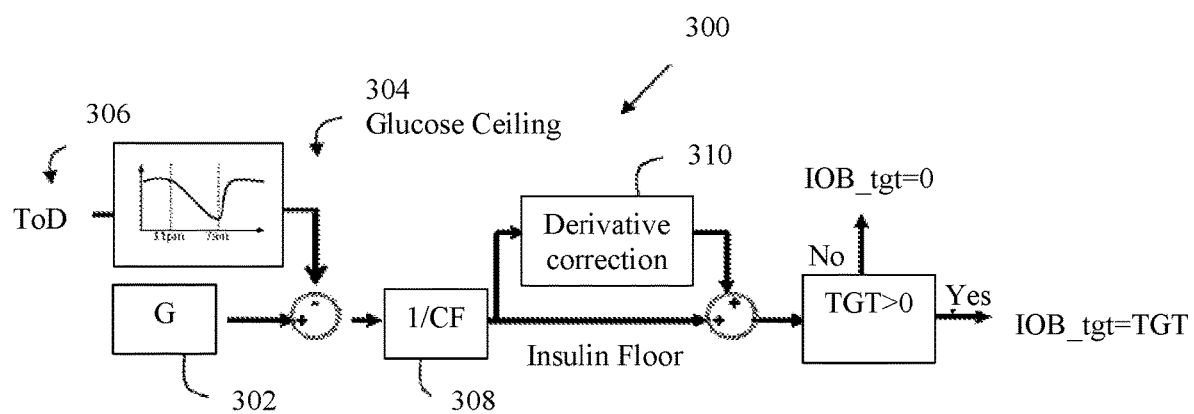
FIG. 3 illustrates and example ISOB controller.

In one example, the Metabolic Monitoring module 108 includes an ISOB controller 300, illustrated in FIG. 3, for computing ISOB. The ISOB computation in this instantiation uses an estimated (or predicted) value of plasma glucose (G) 302 and compares it to a time dependent "glucose ceiling" 304, which varies based on the time of day 306. The difference is then transformed, at module 308, in insulin space using a metric of the patient insulin sensitivity. Such metric could be the patient's own Insulin Sensitivity Factor pattern (ISF, a common insulin pump parameter) or be derived from the past total daily insulin ("1800 rule": ISF=1800/TDI, or "1500 rule": ISF=1500/TDI), from the patient 24h basal dose (TDI=2*TDB), and finally the patient's body weight (TDI=a+b*BW).

In addition, ISOB can be corrected, at module 310, for slope (i.e. predicted ahead in a linear fashion) to react faster to increased need or limit the risk of overdose. These corrections do not have to necessarily be symmetric (i.e. one may choose to limit the correction in one direction more than in the other as below). Similar effect can be achieved by using a predicted glucose instead of an estimated glucose as input. Table 3 illustrates example variables used by the ISOB Controller 300.

TABLE 3

Example variables used by the ISOB Controller

| Name | Description | units | Type |
|------|-------------|-------|------|
| Inputs | | | |
| Time | absolute time at execution time | seconds | UNIX datetime |
| IOB | insulin on board | U | float |
| Gest | estimated glucose. | mg/dl | float |
| basal | basal rate value at execution time | U/hr | float [0-3] |
| CF | Correction Factor at execution time | $mg \cdot dl^{-1} \cdot U^{-1}$ | float [10-100] |
| outputs | | | |
| du | Differential correction rate | $U \cdot min^{-1}$ | Float [0 0.1] |
| parameters | | | |
| DER | FIR filter parameter for short term derivative computation | $min^{-1}$ | 1 × 5 float array fixed at 0.04  0.02  0  −0.02  −0.04 |
| T2tgt | time to achieve IOB target | min | float fixed at 30 |
| PredH | prediction horizon for IOB target correction | min | float fixed at 60 |

Computation:

1. The ISOB Controller 300 computes the time of day using:

$$ToD = (Time - 86400 * floor(Time/86400))/60 \quad \text{Equ(11)}$$

2. The ISOB Controller 300 computes the glucose target using:

$$x = \begin{cases} \dfrac{1 + ToD}{7} & \text{if} \quad y < 6 \\ \dfrac{7 - ToD}{7} & \text{if} \quad ToD \geq 6 \text{ and } ToD < 7 \\ 0 & \text{if} \quad ToD \geq 7 \text{ and } ToD < 23 \\ \dfrac{ToD - 23}{7} & \text{if} \quad ToD > 23 \end{cases} \quad \text{Equ(12)}$$

$$gluc\_tgt = 160 - 45 \times \dfrac{\left(\dfrac{x}{0.5}\right)^3}{1 + \left(\dfrac{x}{0.5}\right)^3} \quad \text{Equ(13)}$$

Figure 4:
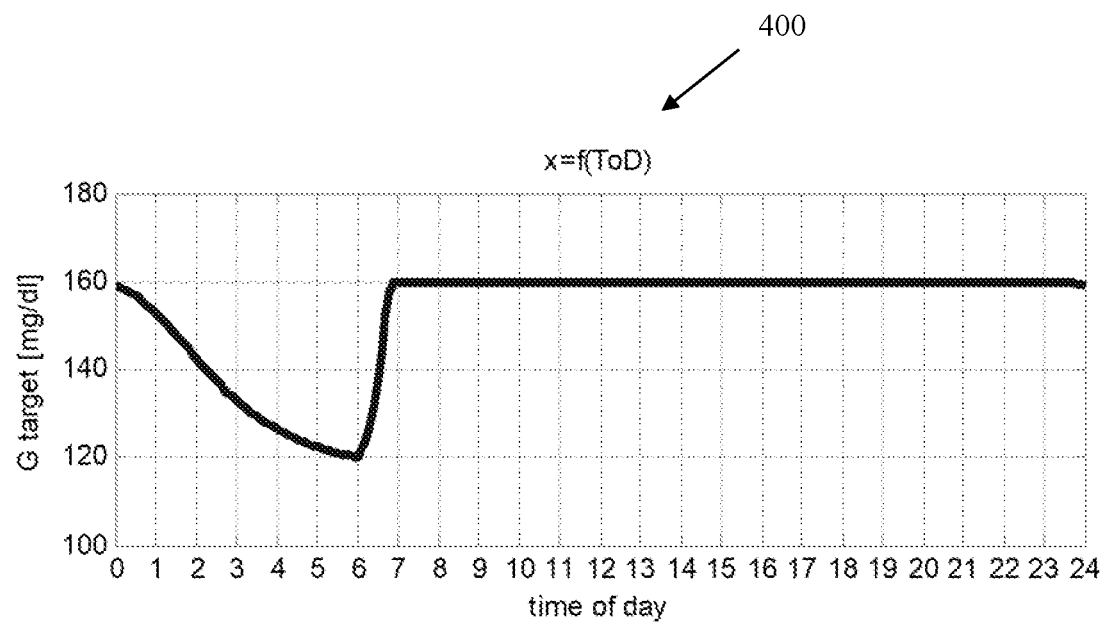
FIG. 4 illustrates a graph of an example transformation resulting from the ISOB controller of FIG. 3.

The resulting transformation is illustrated in the graph 400 of FIG. 4.

The amount of insulin required to achieve that target is computed as:

$$INS_{Target} = \frac{Gest - gluc\_tgt}{CF} \quad \text{Equ(14)}$$

and this variable is extrapolated 1 h ahead ($INS_{Target\_predicted}$) using its current value and first derivative as follows: The slope of the $INS_{Target}$ is computed with a digital FIR filter using the last 5 values of the (easily accessible by back computing gluc_tgt) $INS_{TargetSlope}$. The parameter set for the FIR filter is provided by der $$INS_{TargetSlope_k} = DER \times \begin{bmatrix} INS_{Target_{k-4}} \\ INS_{Target_{k-3}} \\ INS_{Target_{k-2}} \\ INS_{Target_{k-1}} \\ INS_{Target_k} \end{bmatrix} \quad \text{Equ(15)}$$

The variables $INS_{Target}$ and $INS_{TargetSlope}$ are saturated:

$$INS_{TargetSat} = \begin{cases} INS_{Target} & \text{if } INS_{Target} < \frac{90}{strller.CF} \\ \frac{90}{strller.CF} & \text{otherwise} \end{cases} \quad \text{Equ(16)}$$

$$INS_{TargetSlopeSat} = \begin{cases} 1/PredH & \text{if } INS_{TargetSlope} > 1/PredH \\ -10/PredH & \text{if } INS_{TargetSlope} < -10/PredH \\ INS_{TargetSlope} & \text{otherwise} \end{cases} \quad \text{Equ(17)}$$

and combined to get a predicted value for $INS_{Target}$:

$$INS_{Target\_predicted} = INS_{TargetSat} + PredH * INS_{TargetSlopeSat} \quad (18)$$

Fault Detection and Classification
Mild/None Fault Detection

This condition is the default of the system. i.e. if no moderate or severe fault are detected then only mild (or no) faults are present.

Moderate Fault Detection and Advised Rate Computation

Once an insulin need is identified (IOB<ISOB), an aspect of an embodiment of the system 100 (and related method) can compute a rate of insulin needed to remedy this difference within a predetermined amount of time ($\tau$). It is important to note that (i) this rate is supplemental to the patient's basal rate, and (ii) the rate can (and often should) be saturated so as to limit the risk associated with an error in ISOB determination (here twice the basal rate). Finally, the computed rate can be either sent to an insulin pump for implementation either as (i) a temporary basal rate of t minutes (Open Loop mode), or as the control action of an automated closed loop system (in that case the rate will re recomputed at every controller step, and therefore is unlikely to be executed in full as ISOB will be re-estimated at each step); or (2) as a display to the patient for manual implementation.

This value is compared to the available IOB. The difference is divided by a predefined time to target (T2tgt) and further limited to be only positive, after which the units are converted:

$$Rate = \frac{INS_{Target\_predicted} - IOB}{\tau}$$

Figure 5:
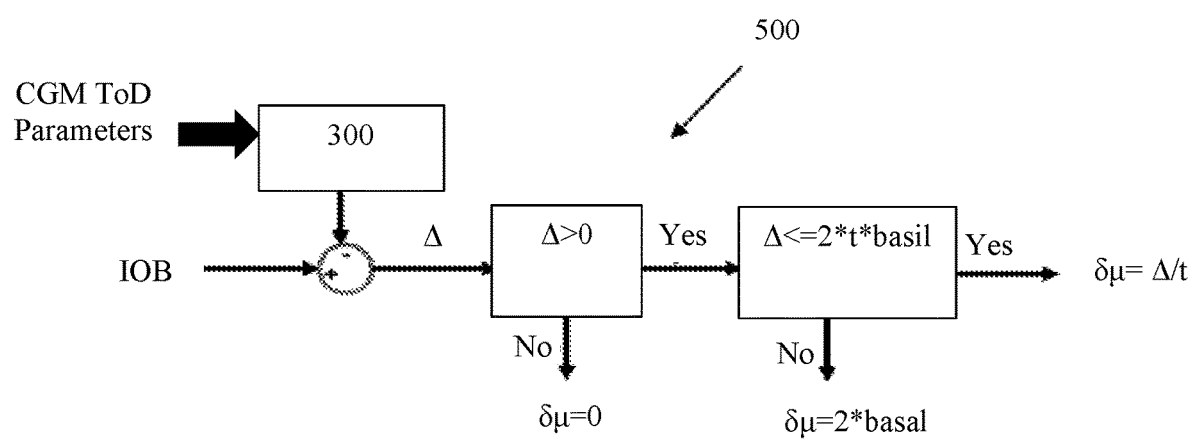
FIG. 5 illustrates example output of the example ISOB controller of FIG. 3.

The output 500 of the module, if use of the IOB controller 300 has been requested, is illustrated in FIG. 5 and defined as:

$$du = \begin{cases} \delta * \frac{basal}{\tau} & \text{if } Rate > \delta * \frac{basal}{\tau} \\ Rate & \text{if } 0 < Rate \leq \delta * \frac{basal}{\tau} \\ 0 & \text{otherwise} \end{cases} \quad \text{Equ(19)}$$

$$\tau = 60; \delta = 2$$

Severe Fault Detection

Severe fault detection is handled differently than moderate fault as it uses an internal variable of the Kalman filter metabolic estimate, instead of the predicted output (glucose). This internal variable is the difference between the feed-forward insulin action (X) and the Kalman filtered insulin action ($\hat{X}$). This variable is an indication of how the internal model agrees with the measurements, which can be used to detect changes indicative of faults in the delivery/monitoring system 100 (e.g. drifting CGM or occluded insulin pump).

The detection is made by comparing the behavior of $\Delta$ the recent past (e.g. one hour) to normative values or its behavior over a longer time period (e.g. 3 h); taking into account that some measured disturbances (such as meals) can greatly affect t $\Delta$. Table 4 illustrates example variables used for severe fault detection.

TABLE 4

Example variables used for severe fault detection

| Name | Description | units | type |
|---|---|---|---|
| inputs | | | |
| Meal Flag | a vector of the past 6 h of the presence of an announced meal in 5 min increments | None | 1 × 72 array of integer [0-1] empty value: 0 |
| Delta | a vector of the past 6 h of the Delta variable from the Meal informed Kalman filter in 5 min increments | min$^{-1}$ | 1 × 72 array of floats no empty allowed |
| outputs | | | |
| Deviation | Quantification of model deviation | None | float [−1 1] |
| Detect | Sever fault detection flag | None | boolean |
| parameters | | | |
| $W_1$ | Width of the short term observation window | min | float fixed at 60 |
| $W_2$ | Width of the short term observation window | min | float fixed at 60 |
| $\omega$ | Controls how long a meal influences the computation | min | Float fixed at 180 |

TABLE 4-continued

Example variables used for severe fault detection

| Name | Description | units | type |
|------|-------------|-------|------|
| N | Controls how sharply the effect of a meal wanes | none | Float fixed at 7 |
| τ | Detection threshold | none | Float fixed at −0.2 |

Computation

First, in an aspect of an embodiment, the system 100 (and associated method) averages the Delta variable over the short term and long term windows:

$$\text{Delta}_{short} = \frac{5}{W_1} \sum^{\frac{W_1}{5}} \text{Delta}\left(72 + 1 - \frac{W_1}{5}, 72\right) \quad \text{Equ(20)}$$

$$\text{Delta}_{long} = \frac{5}{W_2} \sum^{\frac{W_2}{5}} \text{Delta}\left(72 + 1 - \frac{W_2}{5}, 72\right) \quad \text{Equ(21)}$$

How close a meal is will determine how much an aspect of an embodiment of the system 100 (and associated method) trusts the short term average over the long term one to compute this parameters we construct recursively a Meal factor for each 5 minute interval (k) over the last 6 hours (k=1 ... 72)

$$MealF_0 = 0 \quad \text{Equ(22)}$$

$$MealF_{k+1} = \begin{cases} MealF_k + 1 & \text{if Meal } (k+1) = 0 \\ 0 & \text{otherwise} \end{cases} \quad \text{Equ(23)}$$

The meal factor is then transformed in a trust factor (from 0 to 1) using a sigmoidal function:

$$p = \frac{\left(\frac{MealF_{72}}{\omega}\right)^n}{1 + \left(\frac{MealF_{72}}{\omega}\right)^n} \quad \text{Equ(24)}$$

And finally the model deviation is quantified:

$$\text{Deviation} = p * \text{Delta}_{short} + (1 - p) * \text{Delta}_{long} \quad \text{Equ(25)}$$

Detection of a severe fault is done by comparing the deviation to a preset threshold:

$$\text{Detect} = \begin{cases} \text{FALSE} & \text{if Deviation} > \tau \\ \text{TRUE} & \text{otherwise} \end{cases} \quad \text{Equ(26)}$$

Patient Alert Module

Regardless of the new insulin delivery rate being automatically sent to an insulin delivery device or displayed to the patient, the system 100 can also alert the patient of the current risk for hyperglycemia. The present inventors, regarding an aspect of an embodiment, propose a three tiers system of alarm (similar to a stoplight):

Green: no or minimal risk
Yellow: hyperglycemic risk is present, insulin should be increased
Red: Serious hyperglycemic risk, cannot be easily mitigated by increase insulin rate. Possible system failure (e.g. pump occlusion, severe sensor drift, dramatic change is patient metabolism)

Light colors can be determined by a range of algorithms

Figure 6:
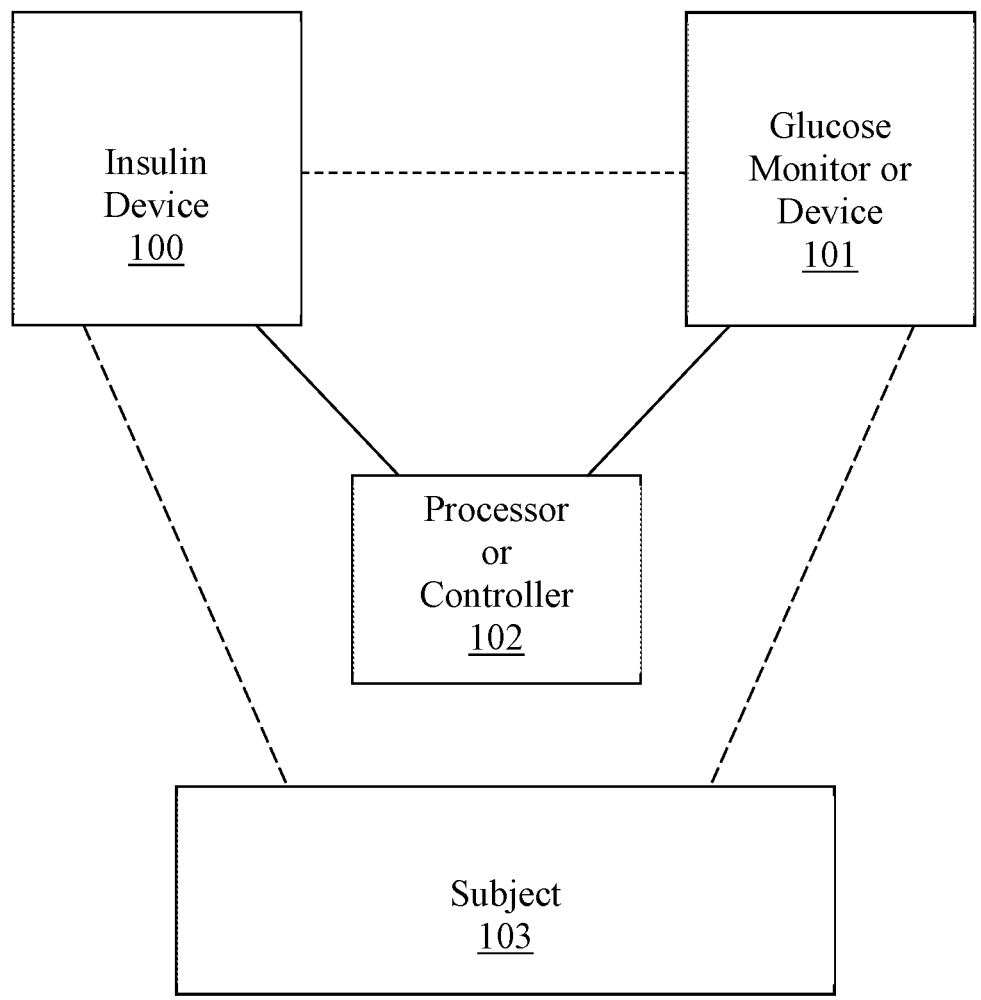
FIG. 6 is a high level functional block diagram of an example glucose monitoring system.

Threshold Based:
G: $IOB < \omega_1$
Y: $\omega_1 < IOB < \omega_2$
R: $IOB > \omega_2$ Glycemic Control Based:
G: $G_{est} < \omega_1$
Y: $\omega_1 < G_{est} < \omega_2$
R: $\omega_2 < G_{est}$ System Action Based
G: no hyperglycemic mitigation needed: $ISOB-IOB < \omega_1$
Y: Hyperglycemic mitigation active: $ISOB-IOB > \omega_1$
R: Hyperglycemic mitigation saturated: $ISOB-IOB > \gamma * basal/\tau$ Red Light Based on System Fault Detection
G: no fault or mild fault
Y: moderate fault
R: Severe fault FIG. 6 is a high level functional block diagram of an example glucose monitoring system. As shown in FIG. 6, a processor or controller 102 communicates with the glucose monitor or device 101, and optionally the insulin device 105. The glucose monitor or device 101 communicates with the subject 103 to monitor glucose levels of the subject 103. The processor or controller 102 is configured to perform the required calculations. Optionally, the insulin device 105 communicates with the subject 103 to deliver insulin to the subject 103. The processor or controller 102 is configured to perform the required calculations. The glucose monitor 101 and the insulin device 105 may be implemented as a separate device or as a single device. The processor 102 can be implemented locally in the glucose monitor 101, the insulin device 105, or a standalone device (or in any combination of two or more of the glucose monitor, insulin device, or a stand along device). The processor 102 or a portion of the system can be located remotely such that the device is operated as a telemedicine device.

Figure 7:
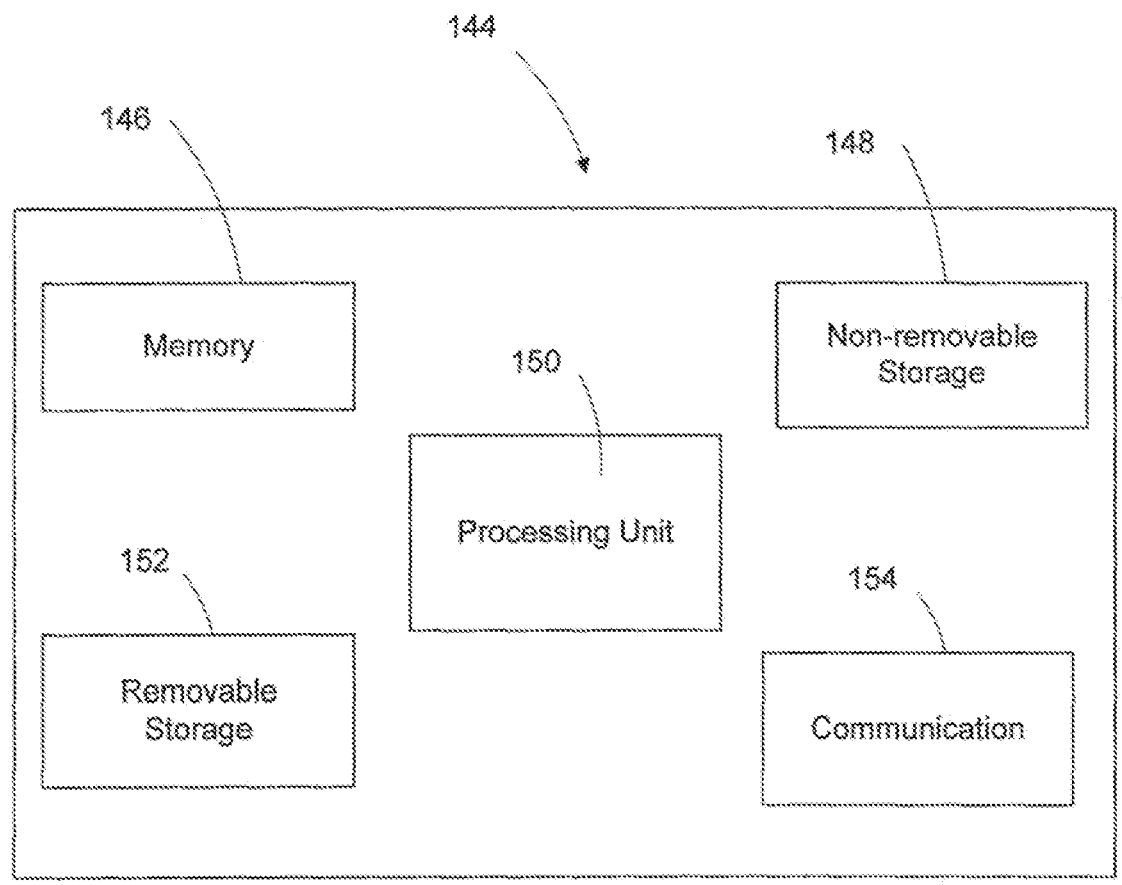
FIG. 7 illustrates a block diagram of an example computer for implementing the example system of FIG. 1.

Referring to FIG. 7, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 8:
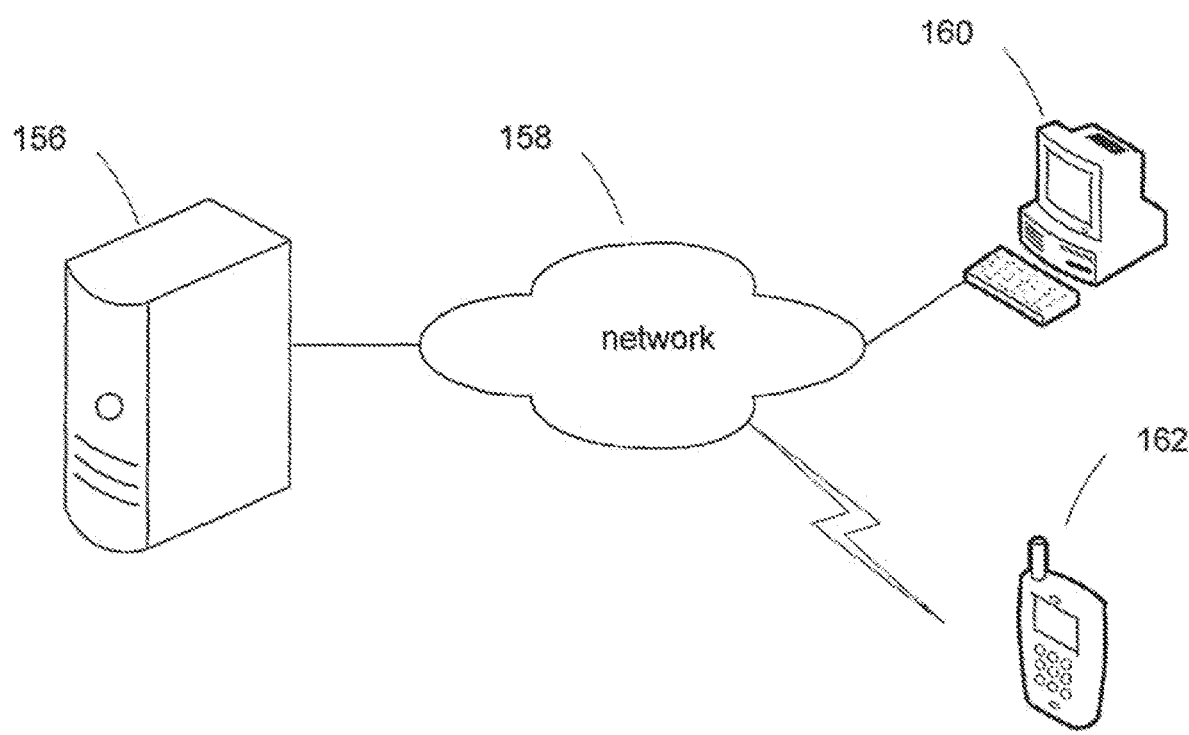
FIG. 8 is an example network system in which embodiments of the example system of FIG. 1 can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 8 illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and/or an insulin device. Any of the components shown or discussed with FIG. 8 may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 9:
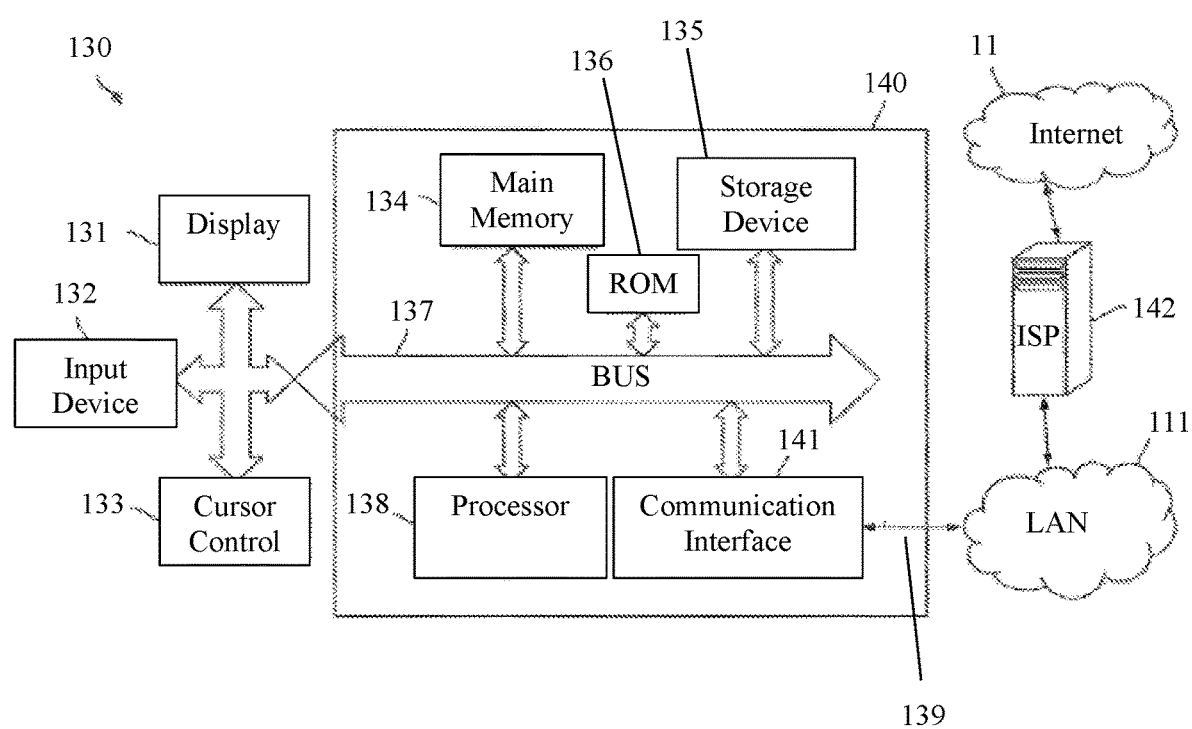
FIG. 9 is a block diagram that illustrates an example computer system and an example associated Internet connection upon which an embodiment may be implemented.

FIG. 9 is a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 9. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 9 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 9 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ac-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of detecting and potentially remedying inappropriate insulin delivery in diabetic patients (or applicable subjects) has been developed; and may be implemented and utilized with the related processors, networks, computer systems, internet, and components and functions according to the schemes disclosed herein.

Figure 10:
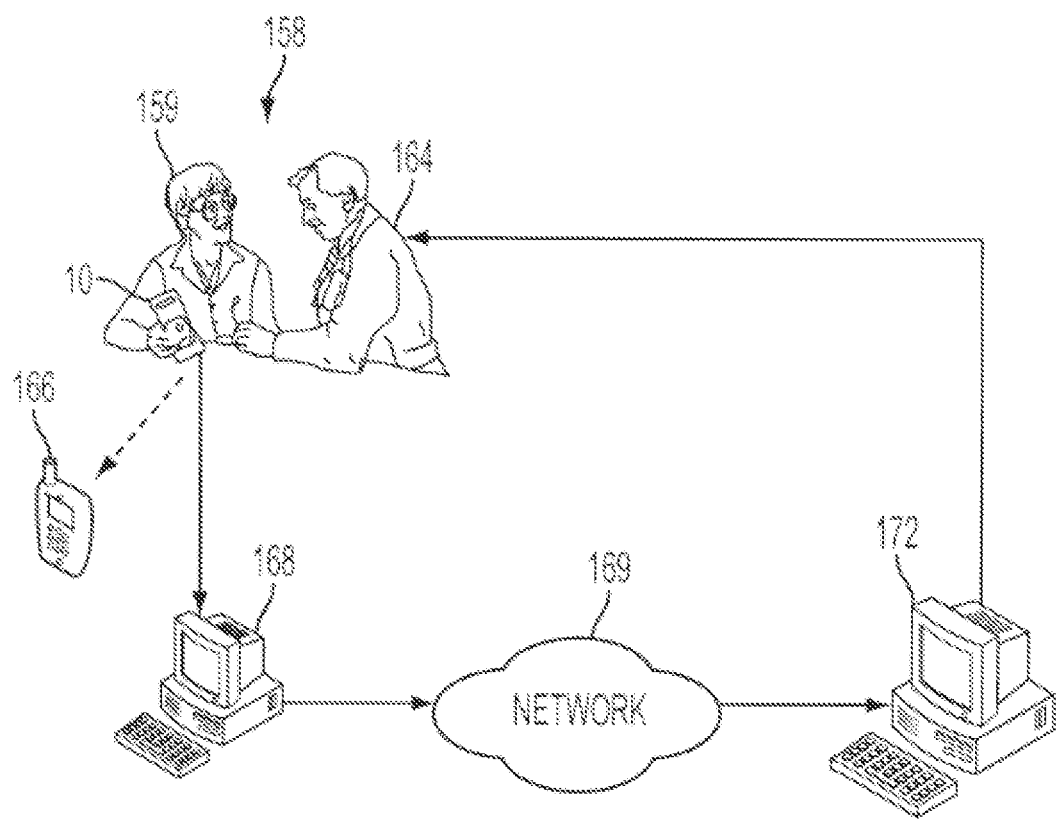
FIG. 10 illustrates a system in which one or more embodiments of the invention can be implemented using a network

FIG. 10 illustrates a system in which one or more embodiments of the invention can be implemented using a network, or portions of a network or computers. Although the present invention glucose device may be practiced without a network.

FIG. 10 diagrammatically illustrates an exemplary system in which examples of the invention can be implemented. In an embodiment the glucose monitor may be implemented by the subject (or patient) locally at home or other desired location. However, in an alternative embodiment it may be implemented in a clinic setting or assistance setting. For instance, referring to FIG. 10, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the invention and any component thereof may be used in the manner depicted by FIG. 10. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 169, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device. An exemplary computing device (or portions thereof) in which examples of the invention can be implemented is schematically illustrated in FIG. 7.

While the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

REFERENCES

The following patents, applications and publications as listed below and throughout this document are hereby incorporated by reference in their entirety herein. It should be appreciated that various aspects of embodiments of the present method, system, devices, article of manufacture, computer readable medium, and compositions may be implemented with the following methods, systems, devices, article of manufacture, computer readable medium, and compositions disclosed in the following U.S. patent applications, U.S. patents, and PCT International Patent Applications and are hereby incorporated by reference herein and co-owned with the assignee (and which are not admitted to be prior art with respect to the present invention by inclusion in this section):

A. U.S. patent application Ser. No. 14/419,375 entitled "Computer Simulation for Testing and Monitoring of Treatment Strategies for Stress Hyperglycemia", filed Feb. 3, 2015.

B. International Patent Application No. PCT/US2013/053664 entitled "Computer Simulation for Testing and Monitoring of Treatment Strategies for Stress Hyperglycemia", filed Aug. 5, 2013; International Patent Application Publication No. WO 2014/022864, Feb. 6, 2014. International Patent Application No. PCT/US2015/010167 entitled "Central Data Exchange Node For System Monitoring and Control of Blood Glucose Levels in Diabetic Patients", filed Jan. 5, 2015.

C. International Patent Application No. PCT/US2014/045393 entitled "Simulation of Endogenous and Exogenous Glucose/Insulin/Glucagon Interplay in Type 1 Diabetic Patients", filed Jul. 3, 2014; International Patent Application Publication No. WO 2015/003124, Jan. 8, 2015.

D. U.S. patent application Ser. No. 14/266,612 entitled "Method, System and Computer Program Product for Real-Time Detection of Sensitivity Decline in Analyte Sensors", filed Apr. 30, 2014; U.S. Patent Application Publication No. 2014/0244216, Aug. 28, 2014.

E. U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.

F. International Patent Application No. PCT/US2007/082744 entitled "Method, System and Computer Program Product for Real-Time Detection of Sensitivity Decline in Analyte Sensors", filed Oct. 26, 2007; International Patent Application Publication No. WO/2008/052199, May 2, 2008.

G. U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.

H. U.S. patent application Ser. No. 14/241,383 entitled "Method, System and Computer Readable Medium for Adaptive Advisory Control of Diabetes", filed Feb. 26, 2014.

I. International Patent Application No. PCT/US2012/052422 entitled "Method, System and Computer Readable Medium for Adaptive Advisory Control of Diabetes", filed Aug. 26, 2012; International Patent Application Publication No. WO 2013/032965, Mar. 7, 2013.

J. International Patent Application No. PCT/US2014/017754 entitled "Method and System for Model-Based Tracking of Changes in Average Glycemia in Diabetes", filed Feb. 21, 2014; International Patent Application Publication No. WO 2014/130841, Aug. 28, 2014.

K. U.S. patent application Ser. No. 14/128,922 entitled "Unified Platform For Monitoring and Control of Blood Glucose Levels in Diabetic Patients", filed Dec. 23, 2013; U.S. Patent Application Publication No. 2015/0018633, Jan. 15, 2015.

L. International Patent Application No. PCT/US2012/043910 entitled "Unified Platform For Monitoring and Control of Blood Glucose Levels in Diabetic Patients", filed Jun. 23, 2012; International Patent Application Publication No. WO 2012/178134, Dec. 27, 2012.

M. U.S. patent application Ser. No. 14/128,811 entitled "Methods and Apparatus for Modular Power Management and Protection of Critical Services in Ambulatory Medical Devices", filed Dec. 23, 2013; U.S. Patent Application Publication No. 2014/0215239, Jul. 31, 2014.

N. International Patent Application No. PCT/US2012/043883 entitled "Methods and Apparatus for Modular Power Management and Protection of Critical Services in Ambulatory Medical Devices", filed Jun. 22, 2012; International Patent Application Publication No. WO 2012/178113, Dec. 27, 2012.

O. U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013; U.S. Patent Application Publication No. 2014/0046159, Feb. 13, 2014.

P. U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

Q. International Patent Application No. PCT/US2010/025405 entitled "CGM-Based Prevention of Hypoglycemia via Hypoglycemia Risk Assessment and Smooth Reduction Insulin Delivery", filed Feb. 25, 2010; International Patent Application Publication No. WO 2010/099313, Sep. 2, 2010.

R. International Patent Application No. PCT/US2013/042745 entitled "Insulin-Pramlintide Compositions and Methods for Making and Using Them", filed May 24, 2013; International Application Publication No. WO 2013/177565, Nov. 28, 2013.

S. U.S. patent application Ser. No. 13/637,359 entitled "Method, System, and Computer Program Product for Improving the Accuracy of Glucose Sensors Using Insulin Delivery Observation in Diabetes", filed Sep. 25, 2012; U.S. Patent Application Publication No. 2013/0079613, Mar. 28, 2013.

T. International Patent Application No. PCT/US2011/029793 entitled "Method, System, and Computer Program Product for Improving the Accuracy of Glucose Sensors Using Insulin Delivery Observation in Diabetes", filed Mar. 24, 2011; International Patent Application Publication No. WO 2011/119832, Sep. 29, 2011.

U. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; U.S. Patent Application Publication No. 2013/0116649, May 9, 2013.

V. International Patent Application No. PCT/US2011/028163 entitled "Method and System for the Safety, Analysis, and Supervision of Insulin Pump Action and Other Modes of Insulin Delivery in Diabetes", filed Mar. 11, 2011; International Patent Application Publication No. WO 2011/112974, Sep. 15, 2011. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012.

W. International Patent Application No. PCT/US2010/047711 entitled "Tracking the Probability for Imminent Hypoglycemia in Diabetes from Self-Monitoring Blood Glucose (SMBG) Data", filed Sep. 2, 2010; International Patent Application Publication No. WO 2011/028925, Mar. 10, 2011.

X. U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; U.S. Patent Application Publication No. 2012/0245556, Sep. 27, 2012. International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; International Application Publication No. WO 2011/028731, Mar. 10, 2011.

Y. U.S. patent application Ser. No. 13/380,839 entitled "System, Method, and Computer Simulation Environment for In Silico Trials in Pre-Diabetes and Type 2 Diabetes", filed Dec. 25, 2011; U.S. Patent Application Publication No. 2012/0130698, May 24, 2012.

Z. International Patent Application No. PCT/US2010/040097 entitled "System, Method, and Computer Simulation Environment for In Silico Trials in Prediabetes and Type 2 Diabetes", filed Jun. 25, 2010; International Application Publication No. WO 2010/151834, Dec. 29, 2010.

AA. U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012.

BB. International Patent Application No. PCT/US2010/036629 entitled "System Coordinator and Modular Architecture for Open-Loop and Closed-Loop Control of Diabetes", filed May 28, 2010; International Patent Application Publication No. WO 2010/138848, Dec. 2, 2010.

CC. U.S. patent application Ser. No. 13/131,467 entitled "Method, System, and Computer Program Product for Tracking of Blood Glucose Variability in Diabetes", filed May 26, 2011; U.S. Patent Application Publication No. 2011/0264378, Oct. 27, 2011.

DD. International Patent Application No. PCT/US2009/065725 entitled "Method, System, and Computer Program Product for Tracking of Blood Glucose Variability in Diabetes", filed Nov. 24, 2009; International Patent Application Publication No. WO 2010/062898, Jun. 3, 2010.

EE. U.S. patent application Ser. No. 12/975,580 entitled "Method, System, and Computer Program Product for the Evaluation of Glycemic Control in Diabetes from Self-Monitoring Data", filed Dec. 22, 2010; U.S. Patent Application Publication No. 2012/0004512, Jan. 5, 2012.

FF. U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

GG. U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

HH. International Patent Application No. PCT/US2001/009884 entitled "Method, System, and Computer Program Product for the Evaluation of Glycemic Control in Diabetes", filed Mar. 29, 2001; International Application Publication No. WO 2001/72208, Oct. 4, 2001.

II. U.S. patent application Ser. No. 12/674,348 entitled "Method, Computer Program Product and System for Individual Assessment of Alcohol Sensitivity", filed Feb. 19, 2010; U.S. Patent Application Publication No. 2011/0264374, Oct. 27, 2011.

JJ. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; U.S. Patent Application Publication No. 2010/0198520, Aug. 5, 2010.

KK. International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; International Patent Application Publication No. WO 2009/009528, Jan. 15, 2009.

LL. U.S. patent application Ser. No. 12/664,444 entitled "Method, System and Computer Simulation Environment for Testing of Monitoring and Control Strategies in Diabetes", filed Dec. 14, 2009; U.S. Patent Application Publication No. 2010/0179768, Jul. 15, 2010.

MM. International Patent Application No. PCT/US2008/067725 entitled "Method, System and Computer Simulation Environment for Testing of Monitoring and Control Strategies in Diabetes", filed Jun. 20, 2008; International Patent Application Publication No. WO 2008/157781, Dec. 24, 2008.

NN. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

OO. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; International Patent Application Publication No. WO2008/067284, Jun. 5, 2008.

PP. U.S. patent application Ser. No. 12/159,891 entitled "Method, System and Computer Program Product for Evaluation of Blood Glucose Variability in Diabetes from Self-Monitoring Data", filed Jul. 2, 2008; U.S. Patent Application Publication 2009/0171589, Jul. 2, 2009.

QQ. International Patent Application No. PCT/US2007/000370 entitled "Method, System and Computer Program Product for Evaluation of Blood Glucose Variability in Diabetes from Self-Monitoring Data", filed Jan. 5, 2007; International Application Publication No. WO 2007/081853, Jul. 19, 2007.

RR. U.S. patent application Ser. No. 12/065,257 entitled "Accuracy of Continuous Glucose Sensors", filed Feb. 28, 2008; U.S. Patent Application Publication No. 2008/0314395, Dec. 25, 2008.

SS. International Patent Application No. PCT/US2006/033724 entitled "Method for Improvising Accuracy of Continuous Glucose Sensors and a Continuous Glucose Sensor Using the Same", filed Aug. 29, 2006; International Application Publication No. WO 2007027691, Mar. 8, 2007.

TT. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; U.S. Patent Application Publication No. 2008/0154513, Jun. 26, 2008.

UU. U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.

VV. International Patent Application No. US2005/013792 entitled "Method, System and Computer Program Product for Evaluating the Accuracy of Blood Glucose Monitoring Sensors/Devices", filed Apr. 21, 2005; International Application Publication No. WO 2005/106017, Nov. 10, 2005.

WW. U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013

XX. International Patent Application No. PCT/US2003/025053 entitled "Managing and Processing Self-Monitoring Blood Glucose", filed Aug. 8, 2003; International Application Publication No. WO 2001/72208, Oct. 4, 2001.

YY. International Patent Application No. PCT/US2002/005676 entitled "Method and Apparatus for the Early Diagnosis of Subacute, Potentially Catastrophic Illness", filed Feb. 27, 2002; International Application Publication No. WO 2002/67776, Sep. 6, 2002.

ZZ. U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005.

AAA. International Patent Application No. PCT/US00/22886 entitled "METHOD AND APPARATUS FOR PREDICTING THE RISK OF HYPOGLYCEMIA", filed Aug. 21, 2000; International Application Publication No. WO 2001/13786, Mar. 1, 2001.

What is claimed is:

1. An insulin monitoring and delivery system, the system comprising:
    one or more processors, one or more non-transitory computer-readable storage devices, and program instructions stored on at least one of the one or more storage devices for execution by at least one of the one or more processors, the program instructions, when executed by the one or more processors, causes the one or more processors to:
        detect presence of a first condition based on comparing feed forward insulin action with a filtered insulin action involving a Kalman filtering technique,
        detect presence of a second condition based on an insulin need, wherein the insulin need is based on comparing insulin that should be on board (ISOB) with insulin on board (IOB), wherein the IOB is based on an amount of insulin active and/or an amount of insulin to be active, and wherein the ISOB is based on an estimation or a prediction of a glucose level;
        upon detecting presence of the first condition or the second condition, classify the detected first condition or second condition into a fault level indicative of a glycemic state; and
        generate a command signal for use by an insulin delivery device to adjust an insulin infusion rate and/or insulin infusion amount based on the fault level.

2. The system of claim 1, wherein the program instructions cause the one or more processors to:
    adjust the insulin infusion rate and/or insulin infusion amount to cause the amount of insulin active to approach the insulin need.

3. The system of claim 1, wherein the program instructions cause the one or more processors to:
    track the IOB.

4. The system of claim 1, wherein the program instructions cause the one or more processors to:
    upon detecting presence of the first condition, classify the detected first condition into a first fault level;
    upon detecting presence of the second condition, classify the detected second condition into a second fault level; and
    classify a third condition into a no-fault level when no first condition and no second condition is detected.

5. The system of claim 4, wherein:
    the first fault level is indicative of severe hyperglycemic risk;
    the second fault level is indicative of moderate hyperglycemic risk; and
    the no-fault level is indicative of little or no hyperglycemic risk.

6. The system of claim 4, wherein:
    the first fault level is indicative of a system failure.

7. The system of claim 6, wherein:
    the system failure is one of a pump occlusion, severe sensor drift, or dramatic change in patient metabolism.

8. The system of claim 4, wherein:
    the second fault level is indicative of a required increase in insulin infusion rate and/or insulin infusion amount for adjusting the insulin infusion rate and/or insulin infusion amount.

9. The system of claim 4, wherein the program instructions cause the one or more processors to:
    indicate the presence of the first fault level, the second fault level, or no-fault level on a display.

10. The system of claim 1, wherein:
    detect the presence of the first condition is further based, at least in part, on one or more of a presence of an unannounced meal, a delta of the filtered insulin action, a delta of recent values to normative values, IOB being greater than a meal influence factor, the meal influence factor being smaller than a plasma glucose level estimation, and/or ISOB-IOB being greater than an amount of basal insulin.

11. The system of claim 1, wherein:
    detect the presence of the second condition is further based, at least in part, on one or more of a first meal influence factor being less than IOB while IOB is also less than a second meal influence factor, the first meal influence factor being less than a plasma glucose level estimation while the plasma glucose level estimation is also less than the second meal influence factor, and/or ISOB-IOB being greater than the first meal influence factor.

12. The system of claim 1, wherein the program instructions cause the one or more processors to:

perform the detecting the presence of the first condition and/or the presence of the second condition within a predetermined time period.

13. The system of claim 1, wherein the program instructions cause the one or more processors to:
adjust the insulin infusion rate and/or insulin infusion amount within a predetermined time period.

14. The system of claim 1, wherein:
the adjusted insulin infusion rate and/or insulin infusion amount is supplemental to a basal insulin need, saturated to reduce a risk associated with an error in determining the ISOB, a temporary basal rate for a predetermined time period, or a control action of an automated insulin monitoring and delivery system.

15. The system of claim 1, wherein the program instructions cause the one or more processors to:
indicate the adjusted insulin infusion rate and/or insulin infusion amount on a display.

16. A computer-implemented method for monitoring and delivering insulin, the method comprising:
detecting presence of a first condition based on comparing feed forward insulin action with filtered insulin action involving a Kalman filtering technique,
detecting presence of a second condition based on an insulin need, wherein the insulin need is based on comparing insulin that should be on board (ISOB) with insulin on board (IOB), wherein the IOB is based on an amount of insulin active and/or an amount of insulin to be active, and wherein the ISOB is based on an estimation or a prediction of a glucose level;
upon detecting presence of the first condition or the second condition, classifying the detected first condition or second condition into a fault level indicative of a glycemic state; and
generating a command signal for use by an insulin delivery device to adjust an insulin infusion rate and/or insulin infusion amount based on the fault level.

17. The method of claim 16, further comprising:
upon detecting presence of the first condition, classifying the detected first condition into a first fault level;
upon detecting presence of the second condition, classifying the detected second condition into a second fault level; and
classifying a third condition into a no-fault level when no first condition and no second condition is detected.

18. The method of claim 17, wherein:
the first fault level is indicative of severe hyperglycemic risk;
the second fault level is indicative of moderate hyperglycemic risk; and
the no-fault level is indicative of little or no hyperglycemic risk.

19. The method of claim 17, wherein:
the first fault level is indicative of a system failure.

20. The method of claim 19, wherein:
the system failure is one of a pump occlusion, severe sensor drift, or dramatic change in patient metabolism.

21. The method of claim 17, wherein:
the second fault level is indicative of a required increase in insulin infusion rate and/or insulin infusion amount for adjusting the insulin infusion rate and/or insulin infusion amount.

22. The method of claim 17, further comprising:
indicating the presence of the first fault level, the second fault level, or no-fault level on a display.

23. The method of claim 16, wherein:
detecting the presence of the first condition is further based, at least in part, on one or more of a presence of an unannounced meal, a delta of the filtered insulin action, a delta of recent values to normative values, IOB being greater than a meal influence factor, the meal influence factor being smaller than a plasma glucose level estimation, and/or ISOB-IOB being greater than an amount of basal insulin.

24. The method of claim 16, wherein:
detecting the presence of the second condition is further based, at least in part, on one or more of a first meal influence factor being less than IOB while IOB is also less than a second meal influence factor, the first meal influence factor being less than a plasma glucose level estimation while the plasma glucose level estimation is also less than the second meal influence factor, and/or ISOB-IOB being greater than the first meal influence factor.

25. The method of claim 16, further comprising:
detecting the presence of the first condition and/or the presence of the second condition within a predetermined time period.

26. The method of claim 16, wherein:
the adjusted insulin infusion rate and/or insulin infusion amount is supplemental to a basal insulin need, saturated to reduce a risk associated with an error in determining the ISOB, a temporary basal rate for a predetermined time period, or a control action of an automated insulin monitoring and delivery system.

27. A non-transitory computer-readable storage medium having stored therein computer-executable instructions that when executed cause at least one processor to:
detect presence of a first condition based on comparing feed forward insulin action with filtered insulin action involving a Kalman filtering technique,
detect presence of a second condition based on an insulin need, wherein the insulin need is based on comparing insulin that should be on board (ISOB) with insulin on board (IOB), wherein the IOB is based on an amount of insulin active and/or an amount of insulin to be active, and wherein the ISOB is based on an estimation or a prediction of a glucose level;
upon detecting presence of the first condition or the second condition, classify the detected first condition or second condition into a fault level indicative of a glycemic state; and
generate a command signal for use by an insulin delivery device to adjust an insulin infusion rate and/or insulin infusion amount based on the fault level.

* * * * *